United States Patent

Lamberti

[11] Patent Number: 6,054,140
[45] Date of Patent: Apr. 25, 2000

[54] LONG ACTING INJECTABLE PARASITICIDAL COMPOSITION AND THE PROCESS FOR ITS PREPARATION

[75] Inventor: Jorge Carlos Lamberti, Buenos Aires, Argentina

[73] Assignee: Biogenesis S.A., Buenos Aires, Argentina

[21] Appl. No.: 09/035,870

[22] Filed: Mar. 6, 1998

[30] Foreign Application Priority Data

Mar. 21, 1997 [AR] Argentina ........................ P970101168

[51] Int. Cl.$^7$ ............................ A01N 25/02; A61K 31/70
[52] U.S. Cl. ............................ 424/405; 514/30; 514/937
[58] Field of Search .................................... 424/405, 486, 424/422; 514/30, 937

[56] References Cited

U.S. PATENT DOCUMENTS

| 4,389,397 | 6/1983 | Lo | 424/180 |
| 5,288,710 | 2/1994 | Cvetovich | 514/30 |
| 5,446,070 | 8/1995 | Mantere | 514/772.6 |

*Primary Examiner*—Neil S. Levy
*Attorney, Agent, or Firm*—Birch, Stewart, Kolasch & Birch, LLP

[57] ABSTRACT

The present invention is drawn to injectable parasitical compositions comprising ivermectin in a 1% (w/w) concentration, benzyl alcohol, polyvinyl pyrrolidone, between 40–65% (v/w) concentration N-methyl-2-pyrrolidone, adjuvants and glycerin until reaching 100% final weight, and methods of making and using the composition.

8 Claims, No Drawings

LONG ACTING INJECTABLE PARASITICIDAL COMPOSITION AND THE PROCESS FOR ITS PREPARATION

It is an object of this invention a new long acting injectable parasiticide composition and the process for its preparation.

Ivermectin is a semisynthetic derivative formed by a mixture of two components, 22,23-dihydroavermectin $B_{1a}$ and 22,23 dihydroavermectin $B_{1b}$. Initial avermectin $B_1$ is a macrocyclic lactone obtained from Streptomyces avermitilis culture fermentation broth and the selective hydrogenation of the existing double bonds in the position C22–C23 of avermectin $B_1$ macrolid structures leads to the synthesis of ivermectin as described in literature.

Ivermectin, a macrocyclic lactone, whose developed formula is:

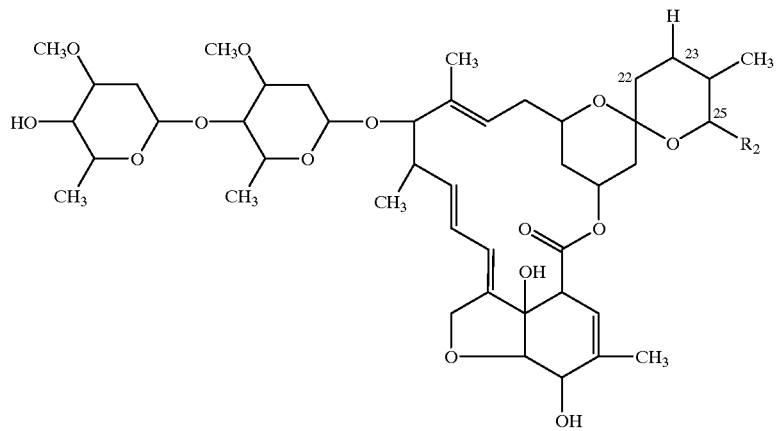

where R2 is isopropyl (20%) or sec-butyl (80%), is a broad spectrum antiparasitic not only against internal parasites, but also against external parasites and even endoparasitic stages of several arthropods. It is active against nemathod genera which affect pets and cattle such as Trichostrongyloidea, Strongyloidea, Metastrongyloidea, Rhabditoidea, Ascaridoidea, Oxyuroidea, Spiruroidea, Filaroidea and Trichurioidea superfamilies. Its high lipo solubility, high body penetration and long term average life account for the broad use of ivermectin as antihelminthic.

The normal way to administer antiparasiticides to large animals is orally. Patents EP 473223, EP 537000, EP 537998 and U.S. Pat. No. 4,440,740 describe solid formulations of ivermectin.

Highly efficient injectable formulations have also been described and their handy application triggered the appearance of a series of preparations, such as the ones described in the following patents which are related with liquid administration forms: EP 146414, EP 413538, EP 535734, EP 538750 and U.S. Pat. No. 4,389,397.

More specifically, patent EP 146414, protects certain non watery liquid formulations which contain ivermectin and more precisely, those which contain ivermectin 1% in a vehicle formed by a mixture of 40% formal glycerol—60% propylene glycol.

The object of the present invention is a novel injectable, long acting parasiticidal composition which contains ivermectin and which presents comparatively superior pharmakinetic properties than known formulations.

Said novel, long acting, injectable parasiticidal composition further presents acceptable levels of residue for the consumption of beef by humans, in conditions of total safety. The European Union has settled maximum residue quantities for ivermectin in bovines at 100 μg/kg in liver and 40 ug/kg in fat.

Likewise, the object of the present invention is a process for the preparation of said novel injectable, long acting parasiticidal composition.

Therefore, the object of the present invention is an injectable, long acting parasiticidal composition which comprises enough ivermectin to achieve a final concentration of about 1% (w/w), bengyl alcohol, polyvinylpyrrolidone, N-metyl-2-pyrrolidone in a 40–65% proportion (v/w) of the total formulation and glycerin until completing final 100% weight.

Besides these components, the formulation may contain stabilizers/antioxidants such as thiodipropionic acid, acetyl cysteine, cysteine, sodium methabisulfite, EDTA, sodium EDTA, sodium citrate, N-propyl gallate, butyl-hydroxy-toluene or a mixture of more than one of these products in a 0.01 to 2% w/w proportion. Optionally, the formulation may also contain a coloring such as betacarotene, in a 0.005–0.05 w/w proportion.

Another object of the present invention is the procedure to prepare an injectable, long acting parasiticidal composition which involves mixing enough ivermectin to obtain a final concentration of about 1% (w/w) with benzilic alcohol and polyvinylpyrrolidone followed by the addition of the mixture to N-metyl-2-pyrrolidone, the latter in a 40–65% proportion (v/w) of the total of the formulation. Afterwards, the antioxidant or mixture of antioxidants dissolved in water if necessary, are added. The mixture is shaken until totally dissolved and glycerin is added until reaching 100% final weight.

Polyvinylpyrrolidone that has been used in the composition of the invention is Kollidon K 17 PF with a K 16–18 value and a relative viscosity of the solution in distilled water at 5% from 1.250–1.370. Kollidon K 17 PF is preferably used in a proportion between 7–11 % (w/w) of the total of the mixture. Benzilic alcohol is incorporated to the mixture in an appropriate proportion to achieve a final concentration between 1.5 and 2% (w/w).

The object of the following examples is to illustrate the invention for a better understanding without trying to introduce limitations.

EXAMPLE 1

Preparation of the Composition 1.000 g of Ivermectin, 8.977 g Kollidon K 17 PF and 1.795 benzyl alcohol in 53.860 ml of N-Metyl-2-Pyrrolidone (Pharmasolve) are dissolved in a stainless steel container. Later, 0.03 g of N-propyl gallate are added. The mixture is shaken until it is totally dissolved. It is taken to 100.000 g with glycerin. The resulting solution is prefiltered and finally filtered in a Nylon 66 or Teflon terminal filter of 0.45 microns pore diameter.

EXAMPLE 2

Pharmakinetic behavior of an Ivermectin 1% w/w in N-Metyl-2-Pyrrolidone and polyvinyl pyrrolidone Composition prepared pursuant to Example 1

6 castrated, male, healthy Argentine Holstein animals were separated. Their weight was between 150–200 kg. The animals were wormed with a benzoimidazolic product 20 days before the start of the test. The composition described in Example 1 was administered to the animals subcutaneously in a rate of 1ml every per each 50 kg of weight. Blood samples were taken in heparinized syringes previously to administration and afterwards following this schedule: 0.5, 1, 2, 3, 4, 5, 6, 7, 8, 10, 12, 15, 20, 25 and 30 days. Plasma was separated by centrifugation and stored until its testing. The trial was performed with high pressure liquid chromatography with ultraviolet detection. Thus, the samples were treated by liquid solid extraction in C18 cartridges. After this process, they were injected in the chromatographer. Ivermectin extraction percentage was 80%. Quantification level of the method was 0.5 ng/ml. Repetitivity had a variation of less than 2% for a 5 ng/ml concentration. Pharmakinetic analysis was performed through a lineal regression program called strip (Brown and Manno, 1978). Pharmakinetic parameters were obtained by classical methods.

Ivermectin concentrations versus time are shown in Table 1. Plasmatic profile of ivermectin can be appreciated in FIG. 1 in which concentration versus time has been represented. The area under curve (AUC) which, in this case, is 300, indicates which percentage of the dosage effectively reaches plasma and contributes to pharmacological action. Pharmakinetic parameters are shown in Table II.

Obtained results show higher plasmatic peaks and plasmatic concentrations that last longer than classical ivermectin preparations such as those prepared in propylenglycolglycerol that were previously mentioned. In this case, an average maximum concentration (Cmax) of 30 ng/ml (Table 1, day 3) and an AUC of 300 (FIG. 1) were found. However, the most distinctive characteristic with respect to said known formulations is found in the midlife of elimination (T½ B in Table II) which in this experience rendered an almost 9 days average, as opposed to the known formulations which have elimination midlives of about 5–6 days. Likewise, concentrations on day 30 in this experiment render a 2.81 ng/ml average while they are 1 ng/ml for classical tioned compositions.

TABLE I

Ivermectin plasmatic concentrations after the administration of a 1% w/w formulation in N-metyl-2-pyrrolidone and polyvinyl pyrrolidone to 6 young bovines - 1 ml every 50 kg.

| HPA | 1 | 2 | 3 | 4 | 5 | 6 | X ± sd |
|---|---|---|---|---|---|---|---|
| 0.5 | 1.21 | 4.70 | 5.60 | 6.60 | 5.38 | 3.72 | 4.70 ± 2.07 |
| 1 | 3.20 | 22.19 | 20.72 | 9.54 | 15.68 | 31.24 | 17.09 ± 9.91 |
| 2 | 8.47 | 23.70 | 25.40 | 18.93 | 23.37 | 21.60 | 20.25 ± 6.17 |
| 3 | 27.15 | 30.56 | 32.56 | 27.68 | 31.54 | 34.61 | 30.68 ± 2.87 |
| 4 | 15.75 | 21.41 | 29.87 | 16.54 | 32.33 | 20.01 | 20.82 ± 5.04 |
| 5 | 18.40 |  | 25.12 | 20.17 | 24.92 | 19.05 | 21.53 ± 3.25 |
| 6 | 22.12 | 21.17 | 22.63 | 15.51 | 19.75 | 20.01 | 20.20 ± 2.56 |

TABLE I-continued

Ivermectin plasmatic concentrations after the administration of a 1% w/w formulation in N-metyl-2-pyrrolidone and polyvinyl pyrrolidone to 6 young bovines - 1 ml every 50 kg.

| HPA | 1 | 2 | 3 | 4 | 5 | 6 | X ± sd |
|---|---|---|---|---|---|---|---|
| 7 | 18.50 | 16.64 | 20.40 | 12.04 | 14.99 | 18.94 | 16.92 ± 3.04 |
| 8 | 15.67 | 12.91 | 19.35 | 10.65 | 12.38 | 11.32 | 13.71 ± 3.26 |
| 10 | 12.17 | 11.92 | 15.21 |  | 11.40 | 10.70 | 12.28 ± 1.73 |
| 12 | 10.93 | 8.66 | 11.57 | 7.62 | 9.34 | 9.81 | 9.66 ± 1.45 |
| 15 | 8.36 | 7.14 | 9.82 | 6.37 | 7.72 | 6.28 | 7.62 ± 1.34 |
| 20 | 6.72 | 4.17 | 7.47 | 2.35 | 5.58 | 3.70 | 5.0 ± 1.94 |
| 25 | 5.60 | 3.42 | 5.94 | 1.24 | 4.31 | 3.44 | 4.0 ± 1.71 |
| 30 | 3.21 | 2.08 | 4.66 |  | 2.40 | 1.69 | 2.81 ± 1.18 |

TABLE II

Pharmakinetic parameters for an Ivermectine 1% w/w preparation in N-metyl-2-pyrrolidone and polyvinyl pyrrolidone in six young bovines after a subcutaneous administration

| Param. | 1 | 2 | 3 | 4 | 5 | 6 | X ± SD |
|---|---|---|---|---|---|---|---|
| A | −64.25 | 19.75 | 96.59 | −5.43 | 101.86 | 7.94 |  |
| α | 0.15 | 0.22 | 0.4 | 0.21 | 0.59 | 0.29 | 0.31 ± 0.16 |
| B | 83.57 | 17.1 | 19.07 | 34.3 | 24.55 | 26.93 | 34.25 ± 24.92 |
| β | 0.11 | 0.07 | 0.047 | 0.13 | 0.077 | 0.093 | 0.09 ± 0.03 |
| Kabs | 0.83 | 2 | 0.68 | 1.05 | 0.89 | 0.64 | 1.02 ± 0.5 |
| T 1/2α | 110.88 | 75.6 | 41.58 | 79.2 | 28.19 | 57.35 | 65.47 ± 29.59 |
| T 1/2β | 6.3 | 9.9 | 14.7 | 5.3 | 9 | 7.5 | 8.8 ± 3.3 |
| T 1/2 abs | 0.84 | 0.35 | 1.02 | 0.66 | 0.78 | 1.08 | 0.79 ± 0.26 |

EXAMPLE 3

Determination of Ivermectin residues after the administration of a 1% w/w Ivermectin Composition in N-metyl-2-pyrrolidone and polyvinyl pyrrolidone prepared in accordance with Example 1.

21 calves between 100–150 kg were separated. The composition identified in Example 1 was subcutaneously administered to them, 1 ml every 50 kg. As from day 0 (administration) 3 animals were put to death weekly from the third to the ninth week.

Plasma, liver, fat, muscle, injected area muscle and kidney samples were taken.

5 g. samples were homogenized in Ultra-Turrax for 2 minutes with 15 ml acetonitrile. The homogenate was centrifugated 5 minutes at 300 rpm. 15 ml of supernatant was transferred to jars and dissolved with water until a 70% watery solution was obtained. 50 µl of triethylamine were added.

C8 bond-Elut cartridges were activated with acetonitrile and acetonitrile: water (30:70). Total sample was passed through cartridge C8. The cartridge was eluted with 5 ml acetonitrile and the eluate was evaporated under nitrogen. The residue was resuspended in 1 ml methanol. Proportional 500 µl were transferred to a silaned tube and evaporated. 100 µl of the deriving agent (1-methyl-imidazole-acetic anhydride-dimethylformamide) (2:6:9) were added and the tube was sent to the oven at 95° C. for an hour. After the cooling, 1 ml chloroform was added, it was subjected to vortical motion and transferred to Sep-Pack cartridges. The cartridge was eluted with 9 ml of chloroform, evaporated and resuspended in 500 μl of methanol and injected in the high pressure system of liquid chromatography with fluorometric detection (HPLC).

Chromatographic conditions were: Mobile stage: acetonitrile: water (97:3); Flow: 1 ml/min.; Excitation: 364 mm.

Results are expressed in ppb as averages of the observed concentrations in every trio of animals, in Table III.

According to residual limits settled by the European Union, experimental animals used in this study showed an average of concentrations in target tissue within the range that is considered acceptable for consumption, as from the 41 following post-administration.

TABLE III

Ivermectin concentrations in several tissues and plasma between the third and ninth weeks post administration of the Composition prepared according to Example 1, in samples of animals treated subcutaneously with 1 ml every 50 kg of weight.

| days | inj. zone. | sartorius | lever | kidney | plasma | fat |
|------|-----------|-----------|-------|--------|--------|-----|
| 21 | 1467.5 | 16.24 | 72.9 | 27.45 | 7.65 | 67.62 |
| 28 | 53.36 | 19.32 | 25.97 | 13.55 | 3.49 | 45.77 |
| 35 | 15.73 | 8.24 | 21.88 | 7.08 | 1.9 | 40.93 |
| 43 | 10.69 | 7.74 | 18.71 | 5.01 | 0.32 | 14.38 |
| 49 | 7.43 | 4.93 | 12.93 | 4 | n.d | 8.4 |
| 55 | 2.01 | 0.72 | 3.21 | n.d. | n.d. | 1.6 |
| 62 | n.d. | n.d. | n.d. | n.d. | n.d. | n.d. |

Having described and determined the nature of the present invention and the way in which it shall be performed, what is claimed as property and exclusive right is:

1. An injectable parasitical composition comprising ivermectin in a 1% (w/w) concentration, benzyl alcohol, between 7–11% (w/w) concentration polyvinyl pyrrolidone, between 40–65% (v/w) concentration N-methyl-2-pyrrolidone, adjuvants and glycerin until reaching 100% final weight.

2. A process for the preparation of an injectable parasiticide composition of ivermectin comprising a) mixing enough ivermectin to achieve a final concentration of 1% (w/w) with benzyl alcohol and polyvinyl pyrrolidone in enough quantity to achieve a final polyvinyl pyrrolidone concentration between 7–11% (w/w), b) adding adjuvants to the mixture of step a);

c) adding the mixture of step b) to N-methyl-2-pyrrolidone, wherein the N-methyl-2-pyrrolidone is in an amount of 40–65% (v/w) proportion of the total of the formulation;

d) shaking the mixture formed in step c) until total dissolution; and e) adding glycerin to 100% final weight.

3. A parasiticide composition in accordance with claim 1, wherein the concentration of benzyl alcohol is 1.5 to 2% (w/w).

4. A parasiticide composition in accordance with claim 1, wherein the adjuvants are antioxidants/stabilizers.

5. A parasiticide composition in accordance with claim 1, wherein antioxidants/stabilizers are selected among thiodipropionic acid, acetyl cysteine, cysteine, sodium methabisulfite, ethylendiaminetetra acetic acid (EDTA), sodium EDTA, sodium citrate, N-propyl gallate, butyl-hydroxy-toluene.

6. Process in accordance with claim 2, wherein sufficient benzyl alcohol is incorporated to reach a final concentration between 1.5 and 2% (w/w).

7. The process in accordance with claim 2, wherein the adjuvants are antioxidants/stabilizers that are selected among thiodipropionic acid, acetyl cysteine, sodium methabisulfite, ethylendiaminetetra acetic acid (EDTA), sodium ethylendiaminetetra acetic acid (EDTA), sodium citrate, N-propyl gallate, and butyl-hydroxy-toluene.

8. Process in accordance with claim 2, wherein the adjuvants that are added are antioxidants/stabilizers.

* * * * *